United States Patent [19]

O'Maleki

[11] Patent Number: 4,904,431

[45] Date of Patent: Feb. 27, 1990

[54] PROCESS FOR MANUFACTURING CATHETERS

[75] Inventor: Samuel L. O'Maleki, Brea, Calif.

[73] Assignee: Baxter International, Inc., Deerfield, Ill.

[21] Appl. No.: 231,037

[22] Filed: Aug. 12, 1988

[51] Int. Cl.$^4$ .............................................. B29C 47/06
[52] U.S. Cl. ..................... 264/103; 156/143; 156/149; 264/139; 264/149; 264/150; 264/167; 264/173; 264/174; 264/159
[58] Field of Search ............... 264/150, 159, 173, 174, 264/149, 139, 209.3–209.5, 167, 103, 209.1; 425/326.1, 380; 156/143, 149

[56] References Cited

U.S. PATENT DOCUMENTS

| | | | |
|---|---|---|---|
| 2,940,126 | 6/1960 | Sheridan | 264/209.1 |
| 4,138,457 | 2/1979 | Rudd et al. | 264/209.1 |
| 4,551,292 | 11/1985 | Fletcher et al. | 264/173 |
| 4,636,346 | 1/1987 | Gold et al. | 264/173 |
| 4,665,604 | 5/1987 | Dubowik | 264/150 |
| 4,753,765 | 6/1988 | Pande | 264/173 |
| 4,764,324 | 8/1988 | Burnham | 264/209.4 |

*Primary Examiner*—Jeffery Thurlow
*Attorney, Agent, or Firm*—Michael C. Schiffer; Sandra S. Schultz

[57] ABSTRACT

A method of manufacturing soft tip catheters having inner rigid polymer layers and outer soft, pliable polymer layers. The method involves first extruding the rigid polymer at varying extrusion rates to form a cylindrical body having a depression at one or more prescribed locations. The outer layer is formed by extruding the soft, pliable polymer over the inner to fill in the depressions. The resulting cylindrical body is then cut to form individual catheters having soft tip as defined by a portion of the prescribed locations.

5 Claims, 1 Drawing Sheet

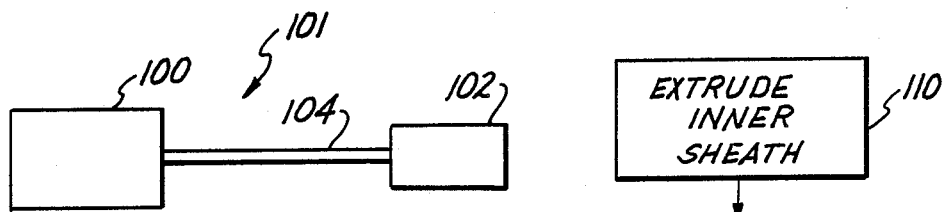
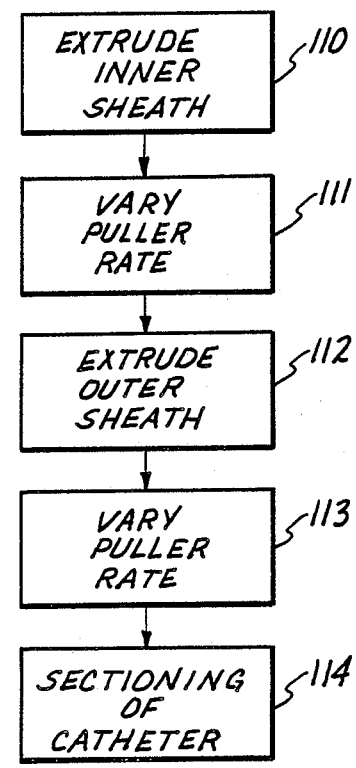
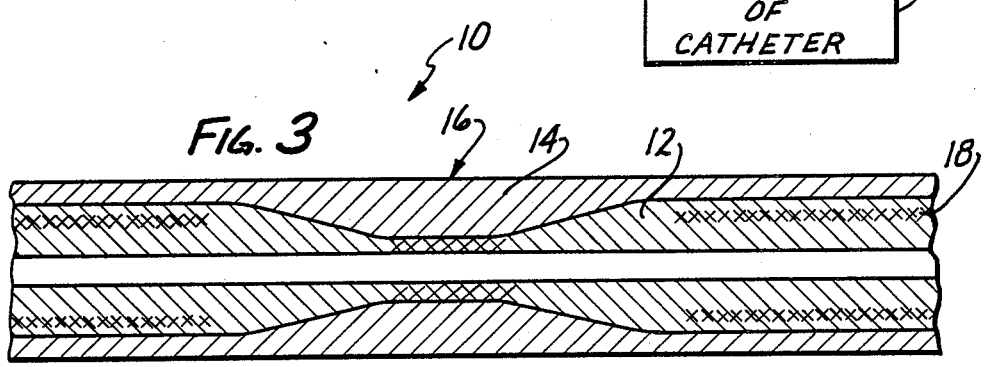
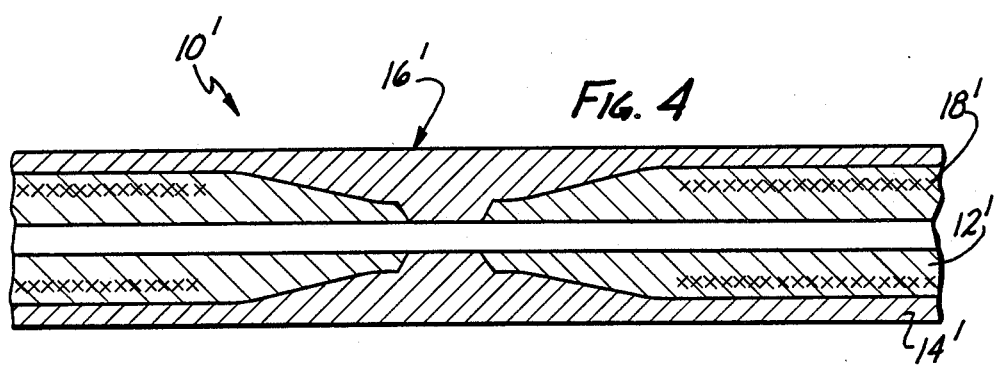

PROCESS FOR MANUFACTURING CATHETERS

BACKGROUND OF THE INVENTION

The present invention is directed to methods of manufacturing soft tip catheters. In particular, the present invention is directed to a method of continuously manufacturing soft tip catheters.

Catheters are used during various surgical procedures for delivering solutions, probes or instruments to specific bodily areas. Depending upon the particular use, the catheter may have one or more internal lumens, or pathways through which the fluid or instrument is inserted. Generally, the catheter is pushed through a blood vessel until reaching the desired site by a twisting motion. In order to promote the ability of pushing the catheter through the blood vessels, the catheter should be rigid, while also possessing sufficient longitudinal flexibility. The combination of these two properties provides the catheter with a high degree of torsional control which allows for the twisting motion.

As the catheter is being pushed through the blood vessel it will come into contact with the vessel wall, and other body organs. The rigidity of the catheter, which is necessary to provide the torsional control, increases the potential of damaging the vessel wall or other body organ. This is particularly true for the catheter distal end, or tip, which may puncture, or in some other manner damage the vessel wall or body organ as the catheter is travelling through the blood vessel. In order to cure this problem catheters have been designed with soft or flexible distal tips to minimize the damage inflicted upon the vessel or organ as the catheter is being pushed through the blood vessel to the desired site.

An example of such a soft tip catheter is disclosed in U.S. Pat. No. 4,402,684, issued to Jessup. The catheter is formed with a soft outer sheath to define a single lumen. The desired rigidity of the catheter is provided by inserting a rigid stylete in the lumen.

This stylete may also be formed to subdivide the lumen into multiple lumens. The soft outer sheath surface minimizes the potential of damaging the blood vessel wall or body organ. The catheter is thus manufactured by first forming the outer sheath, and then by inserting the stylete into the lumen. This type of procedure does not lend itself to any type of automated manufacturing process.

Soft tip catheters are usually manufactured by fusing a flexible tubular portion to the distal end of a rigid catheter body. Examples of these types of catheters are disclosed in U.S. Pat. Nos. 4,563,181 issued to Wijayarathna et al; 3,485,234 and 3,585,707 both issued to Stevens; 4,321,226 issued to Markling; 4,531,943 issued to Van Tassel et al; and 4,665,604 issued to Dobowik. This type of catheter design is also disclosed in U.S. patent application Ser. No. 946,491, filed on Dec. 23, 1986, which is assigned to the same assignee of the instant application, the parent application of U.S. patent application Ser. No. 271,351, filed 11/10/88.

An example of one such fusing process is disclosed in Markling, Dubowik and Stevens, and is known as a lap joint fusing process. The various methods of fusing the soft tip to the distal end of a rigid catheter body, no matter what the specific process entails, does not lend itself to an automated process, and as a result is time and labor consuming.

Other methods of forming soft tip catheters have been developed whereby the catheter is formed with two sheaths, an inner sheath formed from a rigid material and an outer sheath formed from a more flexible material. The outer sheath is extended beyond the inner sheath to form an integral soft tip. Examples of such catheters, and the methods of forming the same are disclosed in U.S. Pat. Nos. 4,239,042, issued to Asai and 4,596,563, issued to Pande.

Another type of catheter construction is disclosed in U.S. Pat. No. 4,636,346 issued to Gold et al. This method involves forming a catheter from three sheaths, an inner sheath formed from polytetrafluoroethylene (PTFE), an intermediate sheath formed from a rigid polymeric material and an outer sheath formed from a more flexible polymeric material. The flexible tip portion is formed by eliminating that portion of the intermediate sheath contiguous to the distal portion of the catheter. Again, this is a complex manufacturing procedure which is time and labor intensive.

While the various discussed catheter construction methods provide adequate soft tip catheters, all suffer from the same disadvantage of being time and labor intensive. In particular, the discussed methods are not adaptable for use in an automated and continuous process.

SUMMARY OF THE INVENTION

The present invention overcomes the above discussed disadvantages by providing a novel method of continuously forming soft tip catheters. The method involves the continuous extrusion of a first rigid polymer to form cylindrical body which will define the inner rigid sheath of the catheter. A second soft, pliable polymer is then extruded over this cylindrical body to form an outer cylindrical layer, which will define the outer soft, pliable sheath of the catheter.

The novelty of the invention is that during the first extrusion step, the rigid polymer is extruded at a variable rate which is altered a prescribed locations to first successively diminish the thickness of the forming layer, and then successively increase the thickness, thus forming a depression. This location will form the tip region of two catheters. The overlaying of this location, during the second extrusion step, with the soft polymeric material will define the soft catheter tip. The final catheters are formed by cutting the resulting structure at the junction of where the thickness of the first forming layer begins to increase in thickness. This juncture is that location at which the first extruded layer is the thinnest. The resulting structure is a cylindrical body having two opposite soft tips, with two catheters being formed by the division of this body.

The resulting catheters can be formed with different lengths by appropriately cutting the cylindrical body in half, at different points along the body length. The final catheters possess integral soft tips, which are defined by the thicker soft, pliable sheath.

DESCRIPTION OF THE DRAWINGS

The present invention may be better understood and its advantages will become apparent to those skilled in the art by reference to the accompanying drawings, wherein like reference numerals refer to like elements in the several figures, and wherein:

FIG. 1 is a schematic illustration of an apparatus useful for carrying out the method in accordance with an embodiment of the invention;

FIG. 2 is a schematic illustration of the method of the invention;

FIG. 3 is a cross-sectional view of a partial length of a cylindrical body illustrating the prescribed location in accordance with an embodiment of the invention; and FIG. 4 is a cross-sectional view of a partial length of a cylindrical body illustrating the prescribed location in accordance with another embodiment of the invention.

DESCRIPTION OF THE INVENTION

The present invention is directed to a method of constructing soft tip catheters. The soft tip catheters prepared by the method of the invention include an inner rigid polymer sheath and an outer soft, pliable polymer sheath. The catheters are formed with a soft distal end which is defined by a gradually tapering inner sheath upon which is formed a gradually thickening outer soft, pliable sheath. This end defines the soft distal tip portion of the catheter.

The method of the invention involves forming a cylindrical body by the extrusion of a soft, pliable polymer over a previously extruded rigid polymer cylindrical body. The soft, pliable polymer will define the outer sheath of the catheter, while the rigid polymer will define the inner catheter sheath. Generally, the thickness of the respective sheath walls is substantially constant along the extruded cylindrical body. However, the extrusion of the rigid polymer is controlled to vary the thickness of the forming inner sheath at one or more prescribed and spatially separated locations along the overall length of the cylindrical extrusion. The thickness of the inner sheath is varied at these prescribed, spaced apart locations to first gradually diminish the layer thickness, and then to gradually increase the layer thickness. In contrast, the extrusion of the soft, pliable polymer is performed to provide that this layer in the thickness is at these spaced apart locations. That is, the resulting outer sheath will be thicker at that location at which the inner sheath is thinnest.

By "rigid polymer" it is meant a polymer which will form a substrate, e.g. the inner sheath having a sufficient shore hardness to provide the desired transverse rigidity and longitudinal flexibility to obtain the necessary torsional control. Typically a shore hardness from about D50 to about D80, preferably a shore hardness of D55 or D63.

Examples of rigid polymers include polyamides, polyethylene terephthlates (PET), polyacetals, polycarbonates and polyether/polyamide co-polymers. These polymers provide the desired transverse rigidity, while also providing longitudinal flexibility.

By "soft, pliable polymer" it is meant a polymer which will render the outer sheath of the catheter flexible and soft enough to avoid trauma to a bodily cavity through which the catheter passes. Typically this polymer will have a shore hardness from about D25 to about D50, preferably a shore hardness of D35 or D40.

Examples of soft, pliable polymers include the various soft thermoplastic polyolefins (polyethylene and polypropylene), polyurethanes, polyesters and other suitable thermoplastic polymers. It should be noted that the polymers used to form the inner and outer sheaths should also be non-thrombogenic, that is biologically compatible materials.

Generally, catheters prepared in accordance with the method of the invention are elongated tubular members having at least one lumen through which fluids, wiring, or electrical devices can be passed. While the present invention will be described by reference to a guide catheter having a single lumen, it should be understood that the present invention is applicable to any soft tip catheter, even a catheter having more than one lumen.

Referring to FIG. 1, a schematic representation of an apparatus for performing the method of the invention is seen generally at 101. The apparatus 101 generally includes an extruder 100, which will normally include a mixing screw leading to one or more dies through which the polymer is pushed, with neither the mixing screw nor dies being shown. Extruding devices do not in and of themselves constitute the invention. As such, no detailed explanation will be provided on the mechanics of such useful devices.

The apparatus 101 further includes a mandrel 104 upon which the polymer is extruded, and any type of device which can be operated to vary the extrusion rate of the polymer from the extruder 100. For example, the apparatus 101 can include a variable speed puller, as seen at 102. Variable speed pullers also do not in and of themselves, constitute the invention, and will thus not be described in any detail.

Basically, variable speed pullers are secured by suitable means, to that end of the polymer extruding out of the extruder 100 to facilitate the drawing of the polymer from out of the extruder 100. The thickness of the polymer being extruded is manipulated by varying the speed at which the polymer is being drawn by the variable speed puller 102. The variable speed puller 102 is operated, in accordance with the invention, to gradually increase and then subsequently decrease the speed of the drawing rate of the polymer through the die of the extruder 100. As will be described more fully herein, the variable speed puller 102 is operated to draw the polymer out from the extruder at varying rates to vary the thickness of the inner and outer sheaths in such a manner so as to define the spatially separated locations described above.

Referring more specifically to both FIGS. 1 and 2, the method of the invention will be described more fully. FIG. 2 is a block diagram schematically illustrating the method of the invention. As seen, the first step 110 is the extrusion of the polymer which will form the inner sheath. Prior to initiating the extrusion of the polymer from out of the extruder 100, the desired polymeric composition is blended.

This polymeric blend will include the specific rigid or soft, pliable polymer depending upon whether the inner or outer sheaths is being extruded. The polymeric blend may also include other components, e.g. pigments, reinforcing materials, fillers, antioxidants or other desired materials.

The prepared polymer blend is placed in the extruder 100, which is then operated to extrude the polymer upon the mandrel 104, e.g. by initiating the turning of the screw, not shown, which advances the polymer blend towards the one or more dies fitted into the opening of the extruder 100, also not shown. During the extrusion step 110, the rigid polymer, which will define the inner sheath, is extruded upon the wire mandrel 104. The rigid polymer is generally extruded at a rate to form a layer having a substantially uniform thickness along the length of the mandrel 104. In step 111 the puller 102 is operated to draw the polymer from out of the extruder 100 at first a faster, and then a slower rate. This will define the locations at which the inner extruded layer will have first a gradually diminishing thickness and then a gradually increasing thickness. By extruding the rigid polymer in this manner discrete depressions are formed at the prescribed locations along the length of the inner sheath layer. More specifically, during step 111 the polymer extrusion speed is, as defined by the rate at which the polymer is drawn by the puller 102, first increased and then decreased, or returned to the original operating speed.

The puller 102 may be operated to form one or more of these depressions at a plurality of prescribed locations along the length of the extruded cylindrical body. The time intervals at which the puller 102 is operated to form the depressions is controlled to provide the depressions at the same or different spaced apart intervals along the length of the cylindrical body.

Next, in step 112, the soft, pliable polymer is extruded over the formed cylindrical body. The extrusion rate of the soft, pliable polymer is also maintained substantially constant. However, at the prescribed locations, at which the depressions are located, the puller 102 speed rate is sufficiently decreased to cause the soft, pliable material to fill in the formed depressions, seen as step 113. Thus the soft, pliable polymer material will be extruded thickest at those locations at which the inner layer is thinnest. The overall thickness of the cylindrical body over its entire length and thus the overall thickness of the formed catheters, will be substantially equivalent.

The depressions formed along the cylindrical body, which have been filled in with the soft, pliable polymer, will define the soft tip portions of the resulting catheters. In order to form these soft tips the resulting cylindrical body is sectioned, as seen in step 114 at the midpoint of each depression. The result is the formation of separate cylindrical bodies having opposite soft tip ends. As stated the mid-point is where the inner layer forming the depressions is the thinnest.

Each of the now formed cylindrical bodies is further sectioned in half to form two separate soft distal tipped catheters. The exact location at which this second sectioning is made depends upon the desired length of the formed catheters. Catheters of different lengths may be formed by the appropriate sectioning the cylindrical bodies formed in the first sectioning step.

The precise number of consecutively formed catheters may vary depending upon the desired length of each catheter, and upon the length of the mandrel upon which the polymer is extruded. The method of the invention may be used to form two or more catheters of equal or different lengths by the appropriate formation of the depressions along the length of the cylindrical body. Other variations of the method would be obvious to one skilled in the art.

Another embodiment of the invention involves the complete removal of the inner rigid polymer layer at the prescribed locations. The resulting cylindrical body will thus not have the above described depressions. Instead individual cylindrical lengths of the inner layer will be formed along the mandrel, with the individual cylindrical lengths being separated from each other for a prescribed distance. This embodiment may be performed by operating the puller 102 to reduce the inner layer at these prescribed locations as much as possible. This will typically leave a film of the rigid polymer, which can easily be removed. Generally, this removal is performed by cutting the polymer away from the mandrel.

The soft, pliable polymer is then laid over the individual cylindrical bodies to fill in the spaces completely. The section of the final cylindrical body is performed as described above, with the resulting catheters having distal ends formed completely from the soft, pliable polymer.

A still further embodiment involves reinforcing the cylindrical bodies with a stiffening material. This increases the rigidity of the resulting catheters. Typically, this stiffening material is wire cord wrapped about the inner layer, and thus becomes embedded between the inner and outer sheaths of the catheter. In accordance with this embodiment the first inner layer is extruded as stated above. Next a wire cord or mesh is wrapped about the formed inner layer. Since it is undesirable to reinforce the soft tip portion in this manner the wire cord or mesh is removed from the prescribed locations, e.g. by cutting. Thus the wire cord or mesh is removed from about the inner layer at the depressions, or at the locations from which the inner layer has been removed as described above. Finally, the soft, pliable material is laid over the wire wrapped inner layer, with the resulting cylindrical body sectioned as described above.

Referring now to FIG. 3, a cross-sectioned side view of a portion of a cylindrical body formed in accordance with the first described method of the invention is seen generally at 10. The illustrated body portion 10 shows one of the prescribed locations at which a depression in the inner layer has been formed. As seen this depression is defined by a gradually decreasing wall thickness followed by the gradual increase in wall thickness, with the depression generally seen at 14. The outer soft, pliable polymer layer, is seen generally at 16. As stated, this layer is extruded over the inner layer to fill-in the described depressions 14. The cylindrical body will be sectioned at the mid-point of this depression 14, where the inner layer is the thinnest. The resulting formed cylindrical bodies have the two opposite soft tip ends. The then formed cylindrical bodies are sectioned to form the resulting soft tip catheters.

Also seen in FIG. 3 is a stiffening material, which is seen as wire mesh 18, which is embedded between the two layers forming the catheter. As stated, this stiffening means is embedded between the inner and outer layers by wrapping the wire mesh 18 about the first extruded layer, and then extruding the second outer layer over the wire mesh 18. Also as stated, the wire mesh 18 is removed at the locations of the depressions 14 prior to extruding the second layer.

Another embodiment is seen in FIG. 4. This is the embodiment where the inner layer is removed from the mandrel to define spatially separated segments. The inner layer 12' is removed from the mandrel, not shown, at the prescribed locations to form individual cylindrical bodies, as defined by the various inner layers 12', which are spatially separated from each layer. The outer layer 16' is extruded over the individual inner layers 12'. The resulting cylindrical body is then sectioned at these prescribed location to form cylindrical bodies having two opposite soft tip ends. These bodies are further sectioned to form the individual catheters. This provides a catheter having a softer tip region than is achieved with the catheter construction method described above, since the ends will be formed solely of the soft, compliable polymer.

As further illustrated, a wire mesh 18' is wound about the inner layer 12'. This wire mesh 18' was wrapped about the inner layer 12' prior to the extrusion of the second outer layer 14'. The wire mesh is also removed from the prescribed locations 16' prior to this second extrusion. During this removal of the wire mesh 18', the desired amount of the inner layer 12' may also be removed. While the preferred embodiments have been described, various modifications and substitutions may be made thereto without departing from the scope of the invention. Accordingly, it is to be understood that the invention has been described by way of illustration and not limitation.

What is claimed is:

1. A process of forming soft tin catheters comprising:
   extruding a first cylindrical layer of a rigid polymer having at one or more prescribed locations a depression formed by said layer first decreasing in thickness and then increasing in thickness;
   extruding a second cylindrical layer of a soft, pliable polymeric material over said first layer, with said first and second layers being extruded to form a cylinder body having a substantially constant thickness; and
   dissecting said cylindrical body first at each of said depressions and further by cutting said formed cylindrical body to form separate catheters, each having the same coefficient of friction extending the entire internal length of each catheter.

2. The process of claim 1 including the steps of embedding a stiffening means between said first and second layers.

3. The process of claim 2 and wherein the catheters are guiding catheters.

4. A process of forming soft tip catheters comprising:
   extruding a first cylindrical layer of a rigid polymer having at one or more prescribed locations a depression formed by said layer first decreasing in thickness and then increasing in thickness;
   removing a portion of said first cylindrical layer at said formed depression;
   extruding a second cylindrical layer of a soft, pliable polymeric material over said first layer, with said first and second layers being extruding to form a cylinder body having a substantially constant thickness; and
   embedding a stiffening means between said first and second layers; and
   dissecting said cylindrical body first at each of said depressions and further by cutting said formed cylindrical body to form separate catheters.

5. The process of claim 4 including the step of removing said stiffening means for each of said prescribed locations.

* * * * *